(12) United States Patent
Madsen et al.

(10) Patent No.: US 9,962,145 B2
(45) Date of Patent: May 8, 2018

(54) SELF-CONTAINED PORT CLOSURE TROCAR AND METHOD OF USE

(71) Applicants: Spencer Madsen, Sandy, UT (US); Mike Fogarty, Provo, UT (US); Paul Johnson, Moab, UT (US); John Langell, Salt Lake City, UT (US)

(72) Inventors: Spencer Madsen, Sandy, UT (US); Mike Fogarty, Provo, UT (US); Paul Johnson, Moab, UT (US); John Langell, Salt Lake City, UT (US)

( * ) Notice: Subject to any disclaimer, the term of this patent is extended or adjusted under 35 U.S.C. 154(b) by 190 days.

(21) Appl. No.: 14/878,777

(22) Filed: Oct. 8, 2015

(65) Prior Publication Data

US 2016/0228107 A1  Aug. 11, 2016

Related U.S. Application Data

(63) Continuation-in-part of application No. PCT/US2014/033813, filed on Apr. 11, 2014.

(Continued)

(51) Int. Cl.
*A61B 17/00* (2006.01)
*A61B 17/04* (2006.01)
*A61B 17/34* (2006.01)

(52) U.S. Cl.
CPC ...... *A61B 17/0057* (2013.01); *A61B 17/0401* (2013.01); *A61B 17/0469* (2013.01); *A61B 17/0482* (2013.01); *A61B 17/3417* (2013.01); *A61B 2017/0046* (2013.01); *A61B 2017/00637* (2013.01); *A61B 2017/00663* (2013.01); *A61B 2017/0409* (2013.01);

(Continued)

(58) Field of Classification Search
CPC ............ A61B 17/0057; A61B 17/0401; A61B 17/0482; A61B 17/0469; A61B 17/3417; A61B 2017/00663; A61B 2017/0046; A61B 2017/00637; A61B 2017/0472; A61B 2017/0414; A61B 2017/0409; A61B 2017/346
See application file for complete search history.

(56) References Cited

U.S. PATENT DOCUMENTS 5,320,632 A   6/1994  Heidmueller
5,364,408 A   11/1994 Gordon
(Continued)

FOREIGN PATENT DOCUMENTS

WO   2011/128392 A1   10/2011

*Primary Examiner* — Julian W Woo
(74) *Attorney, Agent, or Firm* — Durham Jones & Pinegar; Randall B. Bateman; Sarah W. Matthews

(57) ABSTRACT

A self-contained, port-closing trocar and method of use which may include an elongated body having a first end, a second end opposite the first end, and a side wall between the first end and the second end, the body further including at least two channels therein, each of the channels originating near the second end, running parallel to the elongated body, and curving towards and forming an opening in the side wall near the first end. The self-closing trocar may also include at least two needles, each disposed within one of the at least two channels, and a handle insertable into the second end of the elongated body, the handle having at least two needle drivers coupled thereto, each needle driver being insertable into one of the at least two channels and engagable with an end of a needle.

25 Claims, 20 Drawing Sheets

Related U.S. Application Data

(60) Provisional application No. 61/810,876, filed on Apr. 11, 2013.

(52) U.S. Cl.
CPC ............... *A61B 2017/0414* (2013.01); *A61B 2017/0472* (2013.01); *A61B 2017/346* (2013.01)

(56) References Cited

U.S. PATENT DOCUMENTS

| | | | |
|---|---|---|---|
| 5,372,588 A | 12/1994 | Farley | |
| 5,374,275 A | 12/1994 | Bradley | |
| 5,540,704 A | 7/1996 | Gordon | |
| 5,575,800 A | 11/1996 | Gordon | |
| 5,860,991 A | 1/1999 | Klein | |
| 6,063,040 A | 5/2000 | Owen | |
| 6,340,351 B1 * | 1/2002 | Goldenberg | A61B 10/025 403/292 |
| 6,743,241 B2 | 6/2004 | Kerr | |
| 6,960,164 B2 | 11/2005 | O'Heeron | |
| 7,824,419 B2 | 11/2010 | Boraiah | |
| 8,013,244 B1 | 9/2011 | Chumacero | |
| 8,029,518 B2 * | 10/2011 | Goldfarb | A61B 17/00234 606/139 |
| 8,109,943 B2 | 2/2012 | Boraiah | |
| 8,518,059 B2 | 8/2013 | Ringley | |
| 8,647,364 B2 * | 2/2014 | Fiehler | A61B 17/0057 606/213 |
| 9,486,191 B2 * | 11/2016 | Gianotti | A61B 17/0057 |
| 9,636,143 B2 | 5/2017 | Weisbrod et al. | |
| 2003/0105473 A1 | 6/2003 | Miller | |
| 2003/0181924 A1 | 9/2003 | Yamamoto | |
| 2005/0149066 A1 | 7/2005 | Stafford | |
| 2011/0071473 A1 | 3/2011 | Rogers | |
| 2013/0090670 A1 | 4/2013 | Keating | |
| 2016/0000460 A1 | 1/2016 | Weisbrod et al. | |

\* cited by examiner

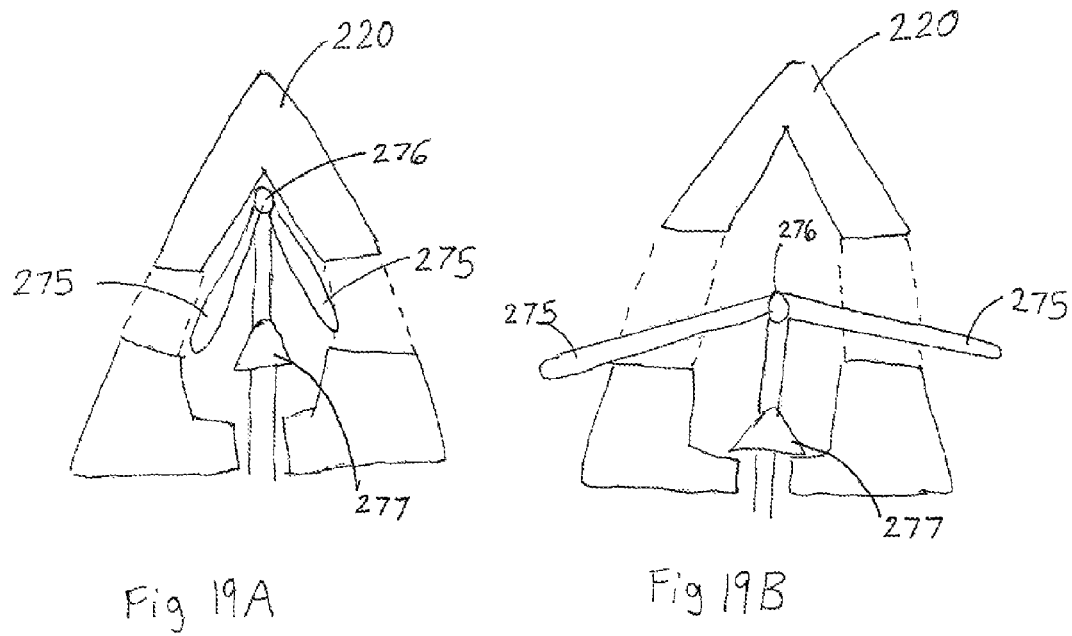

SELF-CONTAINED PORT CLOSURE TROCAR AND METHOD OF USE

THE FIELD OF THE INVENTION

The present invention relates to trocars with closure mechanisms capable of closing a laparoscopic port or incision, in particular a closure mechanism which is contained entirely within the obturator, not requiring specific cannulae.

BACKGROUND

Approximately 2.5 million laparoscopic surgeries are performed each year in the U.S and more than 5 million worldwide. Laparoscopic surgeries insert a device known as a trocar through body tissue, such as the abdominal wall. A trocar consists of two pieces: a central obturator, which comprises a handle and a puncturing tip; and a cannula, which is typically tube-shaped. Once through the abdominal wall the obturator is removed from the cannula and the cannula is left in place, traversing the abdominal wall. The cannula serves as a port that facilitates surgical instruments, endoscopes, and the like, which allow the surgery to be performed inside the abdomen or other body cavity through small incisions in the abdominal wall (FIG. 1). Trocars are typically 5-15 mm in diameter and most surgeries use at least three, including one that is 10 mm or larger to accommodate larger instruments and specimen removal. The wounds left by the larger trocars require closure of the intra-abdominal port to prevent intestinal herniation through the defect in the abdominal wall.

Current methods for closing these larger port sites are either difficult to perform or are cumbersome, can require considerable time to execute, and may place the surgeon at risk for needle sticks. The current "standard of care" for the closure of intra-abdominal defects is performed using a needle attached to suture material and guided through the trasversalis fascia with needle-nosed forceps. Ineffective closure of intra-abdominal defects increases the patient's risk to herniation at the closure site. The consequences of intestinal herniation through a laparoscopic port can be severe, including organ necrosis and intestinal loop rescission.

Additionally, patients with thick abdominal walls increase the difficulty, time, and risk for proper port closure. This often results in misplaced suture and ineffective closure of the port. In 2011, the NIH published a study reporting that patients suffered from trocar site herniation 1.85% of the time on average. The results were highly dependent on surgical technique and complication rates ranged from 0.07% to 22%. Accordingly, there is a need for a consistent method for port closure following laparoscopic surgery.

Several devices have been set forth to address this need, such as U.S. Pat. No. 8,109,943, to Boriah. Boriah discloses a trocar with a specially-adapted cannula shaft, and a obturator, also variously defined as a shaft or port element, which works in conjunction with the cannula to insert suture anchors through the fascia wall. A major drawback to such a device is that the specially-adapted cannula is thicker due to needles and the like contained within, and it must be used. This is problematic, especially if a practitioner wishes to use a cannula with different features, such as thinner walls, lights, irrigation or aspiration mechanisms, or different markings. Further, the specially-adapted cannula must either be left in place during surgery, or the surgery must be performed, the original cannula withdrawn, and then the specially-adapted cannula-obturator inserted in order to close the port—a process resulting in further tissue damage. Because of the complexity of such devices, they are also more expensive to manufacture.

Accordingly, there is a need for a port closure device which is simple, which can be used in conjunction with any type of suitably-sized cannulae, and which is both easy to use and inexpensive to manufacture.

SUMMARY OF THE INVENTION

In one embodiment, the invention may provide a self-contained port closing trocar, including an elongated body having a first end, a second end opposite the first end, and a side wall between the first end and the second end, the body further including at least two channels therein, each of the channels originating near the second end, running parallel to the elongated body, and curving towards and forming an opening in the side wall near the first end; at least two flexible needles, each disposed within one of the at least two channels; and a handle insertable into the second end of the elongated body, the handle having at least two needle drivers coupled thereto, each needle driver being insertable into one of the at least two channels and engagable with an end of a needle.

In another embodiment, the self-contained trocar may include two flexible needles having a free end disposed near the opening at the side wall.

In yet another embodiment the self-contained trocar of may have at least two anchors, each of which is associated with the free end of one of the at least two flexible needles.

In still another embodiment, the self-contained trocar may have a length of suture attached to each of the at least two anchors.

In some embodiments, inserting the handle into the second end of the elongated body may drive each of the at least two flexible needles through an opening in the side wall and out of the elongated body.

In some embodiments, each of the at least two flexible needles may be driven through respective openings on opposite sides of the side wall of the elongated body.

In still other embodiments, the flexible needles may exit at an angle of approximately 45° relative to the elongated body.

In another embodiment, pulling the handle out of the second end of the elongated body may retract each of the at least two flexible needles into one of the at least two channels.

In another embodiment, the end of the elongated body may comprise a bladeless tip.

In still another embodiment, the self-contained port closing trocar may comprise a suture spool disposed at the first end of the elongated body, wherein at least a portion of the length of suture is wound around the suture spool.

In yet another embodiment, the handle of the self-contained port closing trocar may include a gear key, and the gear key either slidingly engages with the needle drivers or lockingly engages with the needle drivers.

In some embodiments, a system of closing openings in fascia walls is disclosed, which may include a self-closing trocar, the trocar including an elongated body having a first end, a second end opposite the first end, and a side wall between the first end and the second end, the body further including at least two channels therein, each of the channels originating near the second end, running parallel to the elongated body, and curving towards and forming a trocar opening in the side wall near the first end, at least two flexible needles, each disposed within one of the at least two channels, and a handle insertable into the second end of the elongated body, the handle having at least two needle drivers coupled thereto, each needle driver being insertable into one of the at least two channels and engagable with an end of a needle; and a cannula configured to receive the self-closing trocar.

According to another aspect of the invention, the self-closing laparoscopic port system may have at least two openings along a length of the cannula, the openings configured to align with the trocar openings in the body.

According to still another aspect, the self-closing laparoscopic port system may include at least one of the cannula and the self-closing trocar having a depth guidance line.

In another aspect of the invention, the self-closing laparoscopic port system, the flexible needles may each have a free end disposed near the trocar opening.

According to another aspect, the self-closing laparoscopic port system may further include at least two anchors, each of which is associated with the free end of one of the at least two flexible needles.

In addition, the self-closing laparoscopic port system may further include a length of suture attached to each of the at least two anchors.

In some embodiments, inserting or pressing the handle into the second end of the elongated body may drive each of the at least two flexible needles through a trocar opening in the side wall and out of the elongated body.

According to still another aspect of the laparoscopic port system, each of the at least two flexible needles may be driven through one of the cannula openings.

Another aspect of the present invention is a suture anchor, which may include an elongated body having a first, pointed end and a second end opposite the first pointed end and an attachment point on the elongated body between the first, pointed end and the second end.

In some embodiments, the second end of the suture anchor may have a concave surface configured to receive a free end of a needle.

According to still another aspect, the suture anchor may have a concave surface which is a conical surface.

In some embodiments, the conical surface of the suture anchor may include a blind channel at an end thereof, the blind channel configured to receive a free end of a needle.

According to another aspect of the invention, the suture anchor may have an attachment point which is an attachment channel having an enlarged cavity at a blind end thereof, the attachment channel being configured to receive a free end of a suture.

In yet another embodiment, the elongated body may be formed partially or wholly of PGLA.

Another aspect of the present invention includes a handle assembly for a self-contained port closing trocar, comprising: a handle having at least two needle drivers coupled thereto, each needle driver being engagable with an end of a needle; at least two flexible needles, each needle being coupled to one of the at least two needle drivers; and at least two anchors, each anchor being engaged with a free end of the at least two flexible needles.

In some embodiments, the handle assembly may further include a length of suture attached to each of the at least two anchors.

According to another aspect of the invention, the handle assembly may include a gear key, which slidably engages with the needle drivers or lockably engages with the needle drivers.

In another aspect, the self-closing trocar may include an elongated body having a first end, a second end opposite the first end, and a side wall between the first end and the second end, the body further including at least two channels therein, each of the channels originating near the second end, running parallel to the elongated body, and curving towards and forming an opening in the side wall near the first end. The self-closing trocar may also include at least two flexible needles, each disposed within one of the at least two channels, and a handle insertable into the second end of the elongated body, the handle having at least two needle drivers coupled thereto, each needle driver being insertable into one of the at least two channels and engagable with an end of a needle.

These and other aspects of the present invention are realized in a port-closing trocar as shown and described in the following figures and related description.

BRIEF DESCRIPTION OF THE DRAWINGS

Various embodiments of the present invention are shown and described in reference to the numbered drawings wherein:

FIG. 19 A-B show alternate constructions of a tip for use with a trocar as disclosed herein.

Figure 1A:
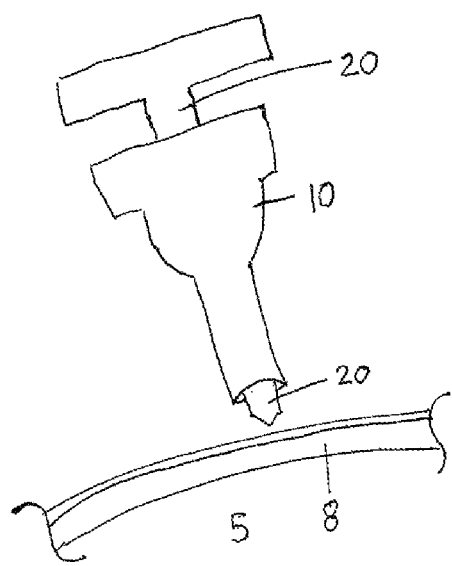
FIG. 1A shows a diagram of a practitioner preparing to perform laparoscopic surgery in an abdominal region of a patient, with a laparoscopic port being opened by a trocar, including a cannula and an obturator.

It will be appreciated that the drawings are illustrative and not limiting of the scope of the invention which is defined by the appended claims. The embodiments shown accomplish various aspects and objects of the invention. It is appreciated that it is not possible to clearly show each element and aspect of the invention in a single figure, and as such, multiple figures are presented to separately illustrate the various details of the invention in greater clarity. Similarly, not every embodiment need accomplish all advantages of the present invention.

DETAILED DESCRIPTION

The drawings will now be discussed in reference to the numerals provided therein so as to enable one skilled in the art to practice the present invention. The drawings and descriptions are exemplary of various aspects of the invention and are not intended to narrow the scope of the appended claims. It will be appreciated that the various aspects of the trocar systems discussed herein may be the same. Different reference numerals may be used to describe similar structures in the various hypodermic needle systems for clarity purposes only.

Various aspects of the invention and accompanying drawings will now be discussed in reference to the numerals provided therein so as to enable one skilled in the art to practice the present invention. The skilled artisan will understand, however, that the methods described below can be practiced without employing these specific details, or that they can be used for purposes other than those described herein. Indeed, they can be modified and can be used in conjunction with products and techniques known to those of skill in the art in light of the present disclosure. Furthermore, it will be appreciated that the drawings may show aspects of the invention in isolation and the elements in one figure may be used in conjunction with elements shown in other figures.

Reference in the specification to "one configuration," "one embodiment" "one aspect" or "a configuration," "an embodiment" or "an aspect" means that a particular feature, structure, or characteristic described in connection with the configuration may be included in at least one configuration and not that any particular configuration is required to have a particular feature, structure or characteristic described herein unless set forth in the claim. The appearances of the phrase "in one configuration" or similar phrases in various places in the specification are not necessarily all referring to the same configuration, and may not necessarily limit the inclusion of a particular element of the invention to a single configuration, rather the element may be included in other or all configurations discussed herein. Thus it will be appreciated that the claims are not intended to be limited by the representative configurations shown herein. Rather, the various representative configurations are simply provided to help one of ordinary skill in the art to practice the inventive concepts claimed herein.

Furthermore, the described features, structures, or characteristics of embodiments of the present disclosure may be combined in any suitable manner in one or more embodiments. In the following description, numerous specific details may be provided, such as examples of products or manufacturing techniques that may be used, to provide a thorough understanding of embodiments of the invention. One skilled in the relevant art will recognize, however, that embodiments discussed in the disclosure may be practiced without one or more of the specific details, or with other methods, components, materials, and so forth. In other instances, well-known structures, materials, or operations may not be shown or described in detail to avoid obscuring aspects of the invention.

Before the present invention is disclosed and described in detail, it should be understood that the present invention is not limited to any particular structures, process steps, or materials discussed or disclosed herein. More specifically, the invention is defined by the terms set forth in the claims. It should also be understood that terminology contained herein is used for the purpose of describing particular aspects of the invention only and is not intended to limit the invention to the aspects or embodiments shown unless expressly indicated as such. Likewise, the discussion of any particular aspect of the invention is not to be understood as a requirement that such aspect is required to be present apart from an express inclusion of that aspect in the claims.

It should also be noted that, as used in this specification and the appended claims, singular forms such as "a," "an," and "the" may include the plural unless the context clearly dictates otherwise. Thus, for example, reference to "a bracket" may include an embodiment having one or more of such brackets, and reference to "the anchor" may include reference to one or more of such anchors.

As used herein, the term "substantially" refers to the complete or nearly complete extent or degree of an action, characteristic, property, state, structure, item, or result to function as indicated. For example, an object that is "substantially" enclosed would mean that the object is either completely enclosed or nearly completely enclosed. The exact allowable degree of deviation from absolute completeness may in some cases depend on the specific context, such that enclosing the nearly all of the length of a lumen would be substantially enclosed, even if the distal end of the structure enclosing the lumen had a slit or channel formed along a portion thereof. The use of "substantially" is equally applicable when used in a negative connotation to refer to the complete or near complete lack of an action, characteristic, property, state, structure, item, or result. For example, structure which is "substantially free of" a bottom would either completely lack a bottom or so nearly completely lack a bottom that the effect would be effectively the same as if it completely lacked a bottom.

As used herein, the term "about" is used to provide flexibility to a numerical range endpoint by providing that a given value may be "a little above" or "a little below" the endpoint while still accomplishing the function associated with the range.

As used herein, a plurality of items, structural elements, compositional elements, and/or materials may be presented in a common list for convenience. However, these lists should be construed as though each member of the list is individually identified as a separate and unique member.

Concentrations, amounts, proportions and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually. This same principle applies to ranges reciting only one numerical value as a minimum or a maximum. Furthermore, such an interpretation should apply regardless of the breadth of the range or the characteristics being described.

The invention and accompanying drawings will now be discussed in reference to the numerals provided therein so as to enable one skilled in the art to practice the present invention. The drawings and descriptions are intended to be exemplary of various aspects of the invention and are not intended to narrow the scope of the appended claims. Furthermore, it will be appreciated that the drawings may show aspects of the invention in isolation and the elements in one figure may be used in conjunction with elements shown in other figures.

FIG. 1A shows a standard laparoscopic procedure, in which a practitioner opens a port through the abdominal fascia 8 and into an abdominal cavity 5, using a trocar 20 comprising a standard cannula or tube 10 and a standard obturator or shaft 12. The standard obturator 12 is bluntly pointed, allowing for it to puncture the abdominal fascia 8. The standard obturator 12 includes a standard obturator handle 14 which permits a better grip, and ensures that the standard cannula 10 does not slide back, and is instead pressed into the abdominal fascia 8 to hold the punctured portion of the abdominal fascia 8 open. The standard cannula 10 may include an insufflation nozzle 11. When the standard obturator 12 is withdrawn, a practitioner may then apply an inert and sterile gas through the nozzle, thus inflating or insufflating the abdominal cavity 5.

Figure 1B:
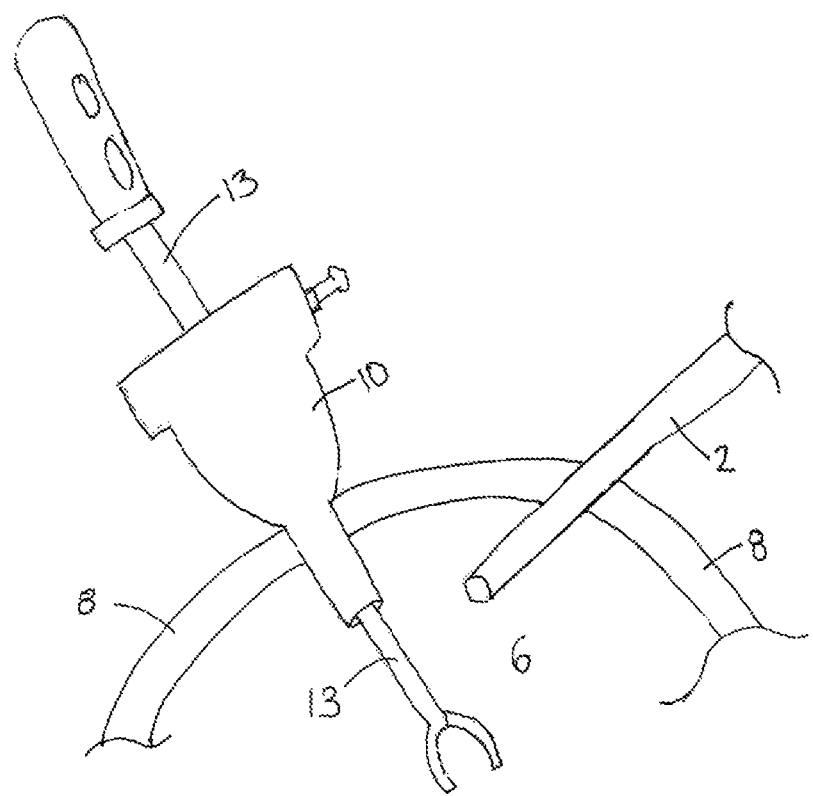
FIG. 1B shows a diagram of a practitioner performing laparoscopic surgery in an abdominal region of a patient, with a laparoscope being inserted through one port and an instrument through another port.

FIG. 1B shows a standard laparoscopic procedure, in which a laparoscope 2 is inserted into a gas-filled abdominal cavity 6. Also pictured is a standard cannula 10 inserted through the abdominal fascia 8. Through standard cannula 10, a medical instrument 13 is inserted in order to perform the medical procedure. Standard cannula 10 may be a variety of sizes, in order to accommodate surgical instruments 13 of varying shapes and sizes. Generally, the smallest standard cannula 10 possible is selected, as this results in the least amount of gas escaping around the medical instrument 13 and the smallest opening in the abdominal fascia 8. Likewise, it is beneficial if the walls of the standard cannula 10 are as thin as possible, in order to minimize tissue damage.

Figure 2:
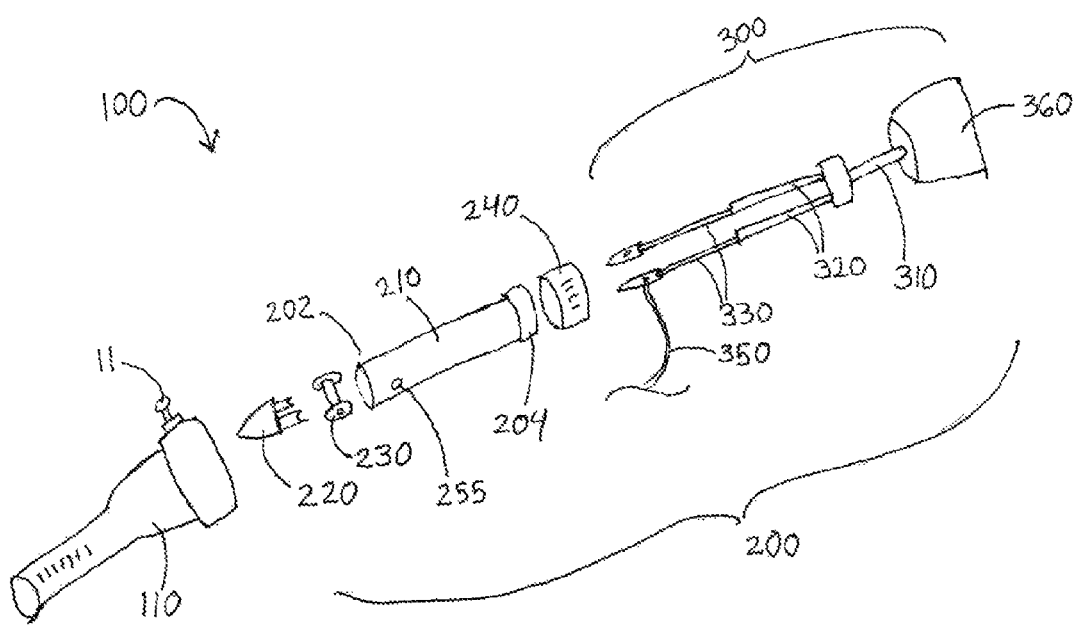
FIG. 2 shows an exploded perspective view of a self-closing laparoscopic port.

FIG. 2 shows an exploded view of one embodiment of a self-closing laparoscopic trocar or port, shown generally at 100, in accordance with the present invention. In the embodiment shown in FIG. 2, the trocar 100 includes a cannula 110 and an obturator, port element, or shaft, shown generally at 200. The cannula 110 is generally a hollow, thin-walled tube, and may be formed from clear or opaque material. The cannula 110 may include an insufflation port or nozzle 11 and may include markings or depth gauges, in order to ensure proper placement.

The obturator 200 of FIG. 2 in various embodiments may include the trocar body or obturator shaft 210, a tip 220 which may be removably attached at a first or distal end 202 of the trocar body 210, a suture spool 230, a cap 240 which may removably attached at a second, proximal end 204 of the trocar body 210, and a handle assembly, shown generally at 300. The trocar body or obturator shaft 210 may be formed of material which is sufficiently rigid to withstand the strong pressing force of being driven by hand through an abdominal fascia, and may be clear in order to allow a practitioner to view the progress through an abdominal fascia. The tip 220 may be bluntly wedge-shaped, in order to facilitate insertion through an abdominal fascia, and may be removable or may be formed in one part with the obturator shaft or trocar body 210. The suture spool 230 may be a cylinder, bobbin, wheel, reel, or spindle, or it may be for example a hollow space for storage of coiled or folded thread. The suture spool 230 may be a removable insert or cartridge, such as a dowel or a ridged plate to separate the string or suture cavity from the rest of the internal workings of the trocar body, for example, or may be formed integrally with the rest of the trocar body. It will be appreciated that the suture spool or cartridge 230 may be positioned distally below the openings 255 or proximally above the openings 255 (See FIG. 3). The number of suture spools 230 may be equal to or fewer than the number of anchors 340. The cap 240 may be removably attached to the obturator shaft 210 and the handle assembly 300 by, for example, threads, a combination of flanges and rings, luer lock, rubber seal, or other means known to one of skill in the art. The cap 240 may also be formed integrally with either the shaft 210 or the handle assembly 300—or both, if it is not desirable that a practitioner be able to disassemble the obturator device 200. The cap 240 may also comprise markings or labeling, so that a practitioner can easily see how the handle assembly 300 is oriented with regard to the rest of the obturator shaft 210. The cap 240 may also comprise a flange, a luer lock, threads, a rubber ring, or other protrusion adapted to engage with the cannula 110, preventing the cannula 110 from being twisted out of alignment with the obturator shaft 210.

The handle assembly 300 may include a handle 360 coupled to an action stage mechanism 310 which is engaged with a pair of needle drivers 320 in a manner that permits coupling and decoupling of the action stage mechanism 310 from the needle drivers 320, e.g. by rotating the handle 360. The action stage mechanism 310 may be, for example, a key gear, a click device, a releasable spring, a slotted ring, a spring-loaded or track-driven mechanism, or other means of cycling through various stages or actions of the device. In embodiments where the action stage mechanism 310 is a key gear or track-driven mechanism, for example, the needle drivers 320 cannot be engaged until the handle is pressed or pulled and twisted to the correct orientation, which may be shown by markings on the cap 240. This prevents the needles, wires, or probes 330 from being deployed until the obturator shaft 210 has reached the appropriate depth as judged by the practitioner, and allows the practitioner to cycle conveniently through the different modes of action of the device.

Each of the needle drivers 320 may be in communication with a needle, wire, or probe 330, and each needle 330 may have an anchor 340 in releasable communication with a free end thereof; the free ends of the needles 330 may be flat, rounded, or pointed. The needles, wires, or probes 330 may be round in cross-section, or may be flattened strips or ribbons of plastic or other material to reduce any possibility of twisting as the needles or probes 330 are driven through tissue. Each anchor 340 has a length of suture 350 attached thereto. Needle 330 may be substantially flexible to adapt to the shapes of the anchor channels 250 (shown in FIG. 3), while retaining sufficient stiffness to push the anchors 340 through the patient's tissue. In one embodiment the needles 330 may be made from a flexible alloy such as nitinol (nickel-titanium), although other materials may also be used. Although the needles 330 may vary in length according to the particular embodiment, in some embodiments the needles are approximately 30-90 mm in length. Needle driver 320 may be substantially rigid, and while the dimensions of the needle drivers 320 may vary depending on the particular embodiment, in some embodiments the needle drivers 320 may consist of cylindrical rods approximately 57 mm long and 2.75 mm in diameter. The needle drivers 320 may be formed integrally with the needles, wires, or probes 330.

In some embodiments, each anchor 340 may be formed from a biocompatible or bioabsorbable material, such as polymer polylactic acid (PLA), or hydroyxapatite (HA), so that they dissolve slowly as the abdominal fascia heals after surgery. Likewise, the suture thread 350 may be formed of a bioabsorbable material, such as polygalactin, polydioxanone, or poliglecaprone. The suture thread 350 may extend from the suture spool 230, which may be located in the handle or in the trocar body 210. In certain embodiments, the anchor 340 is made of PGLA (glycolide-co-L-lactide) an absorbable copolymer of lactic and glycolic acid, due to its absorbable qualities and biocompatibilities. In one particular embodiment, the suture 350 may be made of polylacticacid/polycycolicacid, although other materials may also be employed. In still other embodiments, the anchor 340 and suture 350 may each be made from the same or different materials. In some embodiments, one or more anchors 340 may be coated with a more quickly-dissolving biocompatible material, or with different biocompatible materials. This surface layer, coating, or film may be thicker in the middle and tapered toward the outer edges, or it may be of uniform thickness.

One advantage of this particular embodiment of the trocar shaft 200 is that both the anchors 340 and the suture thread 350 are contained entirely within the trocar body 210, without need for hanging lengths of suture thread 350. Thus the device may be assembled and packaged all in one unit, without exposing either bioabsorbable material to potentially-corrosive air or humidity until the device is deployed in surgery.

Some embodiments of the trocar may include more than two needles 330 and needle drivers 320. Additionally, some embodiments of the anchor 340 may be, for example, spear-head-shaped, flanged, ridged, or otherwise shaped so that once pushed into an abdominal cavity, they cannot easily stick to the needle 330 and be withdrawn with the needle, wire, or probe 330. The suture thread 350 may be attached to the anchor 340 at any point, and may be formed integrally with the anchor 340, or may pierce through the anchor 340 and loop around it, for a secure connection.

Figure 3:
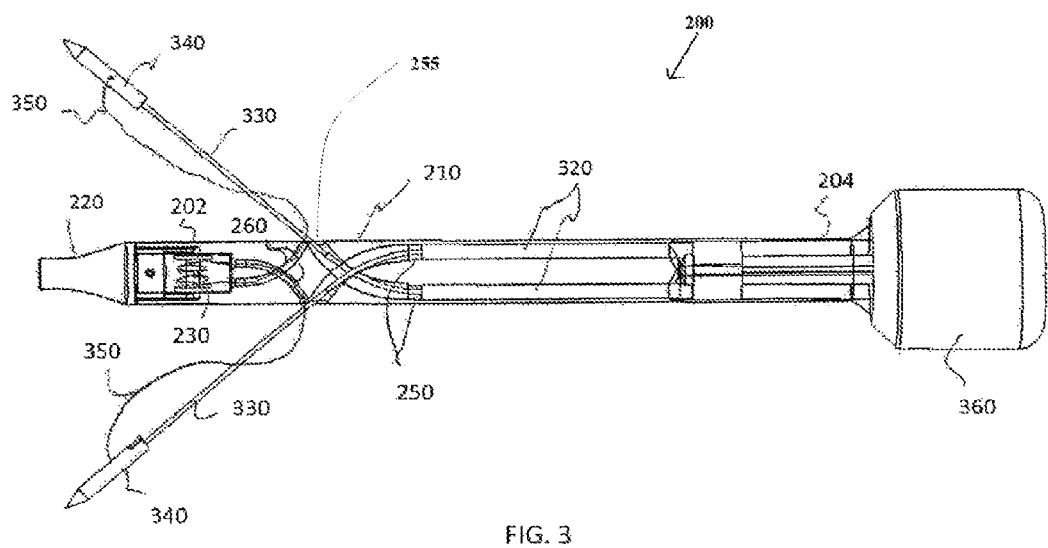
FIG. 3 is a side view of a trocar for a self-closing laparoscopic port.

FIG. 3 is a cut-away side view of a fully-assembled obturator shaft, indicated generally at 200. The trocar or obturator body 210 includes two anchor channels 250, each of which terminates at an opening 255 near the tip 220 of the trocar body 210. Each of the anchor channels 250 extends parallel to the long axis of the trocar body 210 and then curves near the tip 220 to terminate at an opening 255 on the side of the trocar body 210. The present embodiment displays two anchor channels 250 but there may be, for example, a number of anchor channels 250 equal to or greater than the number of needles 330. To maximize the radius of curvature, each anchor channel 250 may be configured to exit the side of the trocar body 210 opposite to the side on which the anchor channel 250 runs, although other configurations are also possible. Generally the exit points or openings 255 of the channels near the tip 220 or first, distal end 202 are on opposite sides of the trocar body 210 so that, ultimately, the sutures 350 are placed on approximately opposite sides of the opening in the patient's tissue, which optimizes closure and healing of the opening in the abdominal fascia.

Figure 11A:
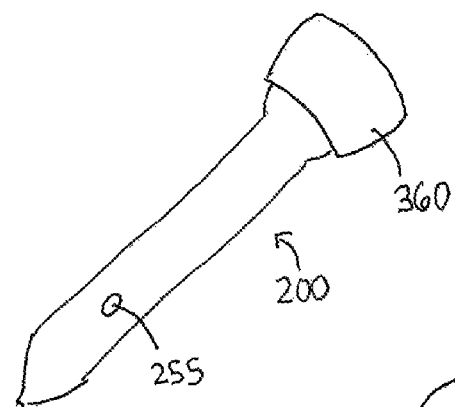
FIG. 11A is a perspective view of a trocar prior to use with the anchors inside of the trocar body.

The needles 330 and needle drivers 320 are inserted into the anchor channels 250 at the second end 204 (FIGS. 2, 3) or at the cap 240 (FIG. 2). The needles 330 are advanced into the anchor channels 250 to a point where the free ends of the needles 330 are still contained within the anchor channels 250 and are engaged with the anchors 340. Prior to use, each of the anchors 340 may be located within one of the anchor channels 250, generally at or near the opening near the first end 202 or the tip 220 of the trocar body 210 (FIGS. 3, 11A). Prior to use, the needles 330 may already be engaged with the anchors 340, or may be separate from the anchors 340.

Prior to use, each length of suture 350 connected to a respective anchor 340 may be wound around the suture spool 230, which may be located at the first end 202 near the tip 220 of the trocar body 210. The remaining portion of the suture 350 that is not wound around the suture spool 230 then leads to the anchor 340. In some embodiments, the trocar body or obturator shaft 210 includes one or more suture channels 260 through which the suture 350 is fed from the suture spool 230 to the anchor 340. In certain embodiments, the suture channels 260 terminate on the side of the trocar body 210 in a location immediately adjacent to and continuous with the ends of the openings 255 of the anchor channels 250. Thus, prior to use, the lengths of suture 350 can be fed to the anchors 340 without protruding from the side of the trocar body 210. Once the suture spool 230 and suture 350 have been properly configured, the tip 220 can be removably or non-removably attached to the first end 202 of the trocar body 210.

Figure 4:
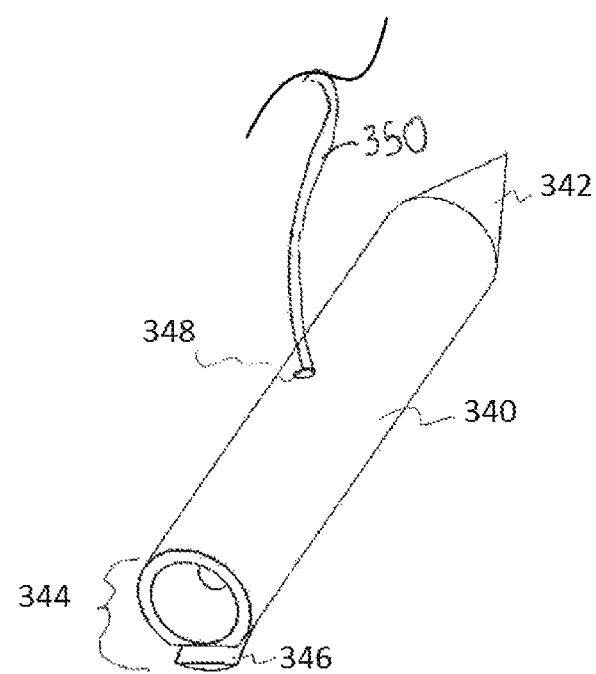
FIG. 4 is a perspective view of an anchor.

FIG. 4 displays one embodiment of an anchor 340. In various embodiments, the anchor 340 may have a pointed end 342 for penetrating tissue and a dimpled end 344 which may be partially-hollow or sleeve-like for engaging the needles 330 (shown in FIG. 3). The dimpled end 344 may include a flap 346, for example a portion of material protruding outward, to help the anchor 340 engage with and remain inside of the anchor channel 250 (shown in FIG. 3) before the device is used. The flap 346 may also be a flexible flange or bulb which is larger than the diameter of a needle 330 (shown in FIG. 3) and thus prevents the anchor from being drawn back into the hole created by the deployment of needle 330 (shown in FIG. 3). The anchors 340 also include an attachment point 348 such as a hole to which a length of suture 350 is attached. In some embodiments, the attachment point 348 is a hole extending through the thickness of the anchor 340, through which the suture material 350 may be inserted and tied. Such embodiments may include a belt-like groove or ridge (not shown) extending radially around the anchor 340, for more stable positioning of the suture thread 350.

The attachment point 348 may be generally located near a midpoint of the anchor 340. One advantage of attaching the suture thread 350 to the anchor 340 near a midpoint is that the anchor 340 will be pulled sideways against the very small opening left by the needle 330 as it withdraws. Thus, the anchor 340 cannot be easily tugged through the abdominal wall.

Figure 5:
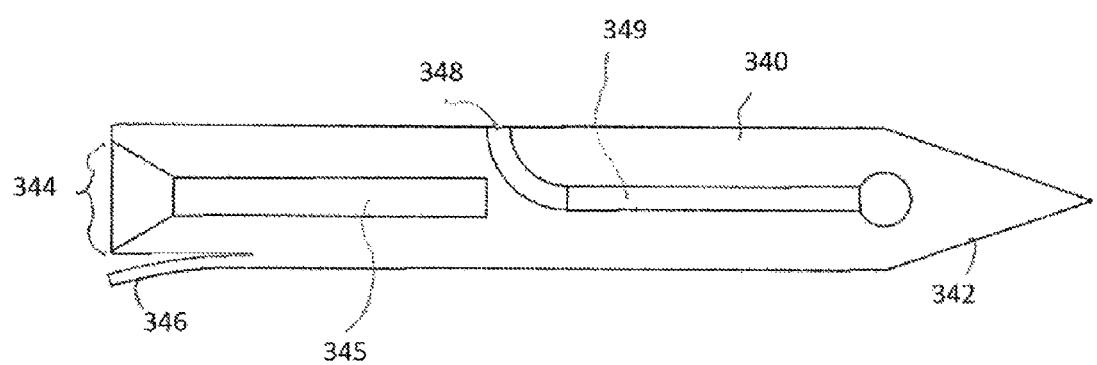
FIG. 5 is a cross-sectional view of an anchor.

FIG. 5 displays an alternate embodiment of an anchor 340. The attachment point 348 may be continuous with an attachment channel 349, where the attachment channel 349 may include an enlarged portion at a pointed end 342 to facilitate secure attachment of suture 350 (e.g. to hold the end of the suture 350 using a knot or a drop of adhesive). The dimpled end 344 in various embodiments may have a conical, rounded, or other concave shape and may include an additional blind channel 345 in which the needle 330 (Shown in FIG. 3) may be inserted.

In still other embodiments, the end of the anchor 340 opposite the pointed end 342 may be flat or may have a convex shape. In use, the free ends of the needles 330

(shown in FIG. 3) are placed against the ends of the anchors 340 opposite the pointed ends 342 in a manner that permits the needles 330 to push the anchors 340 through the tissue and to then detach and leave the anchors 340 and suture 350 in place when the needles 330 are retracted.

Although the sizes and shapes of the anchors 340 may vary, in some embodiments the anchors 340 are cylindrical rods approximately 21 mm in length and 3 mm in diameter. It will further be appreciated that a coating or film (not shown) of biodegradable material may be applied to the anchor either before or after the suture material 350 is attached to the anchor 340, in order to improve adherence of the suture 350 to the anchor 340.

Figure 6A:
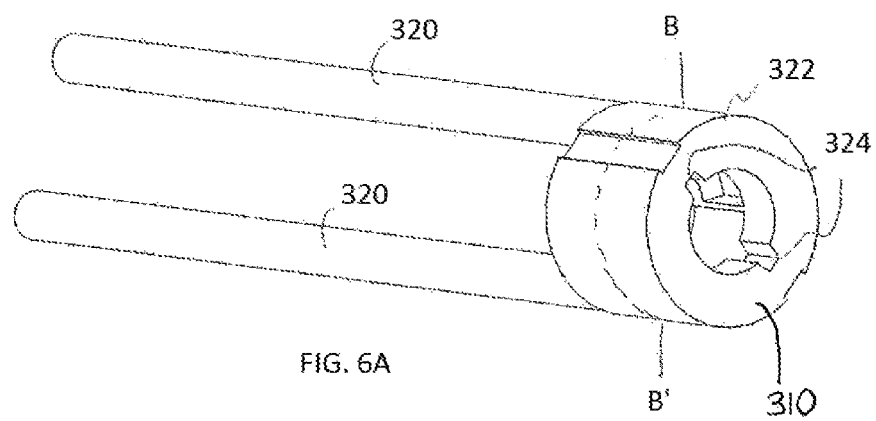
FIG. 6A is a perspective view of one embodiment of a needle driver.
Figure 6B:
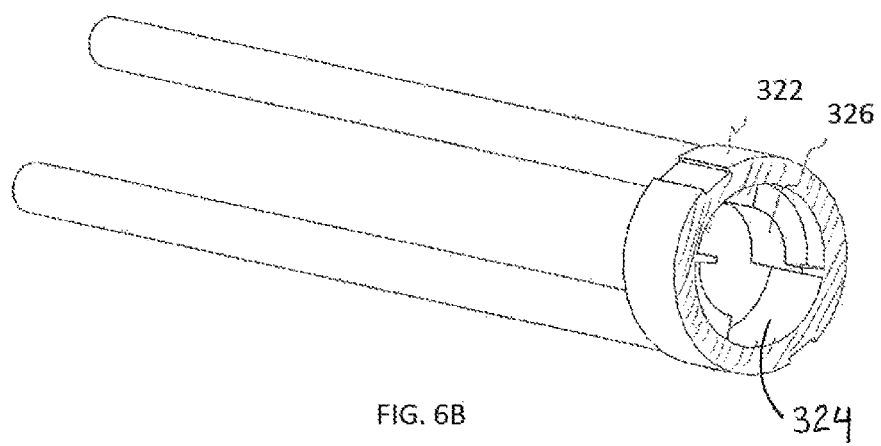
FIG. 6B is a perspective view of one embodiment of a needle driver cross-sectioned at the line indicated by B-B' in FIG. 6A.
Figure 7:
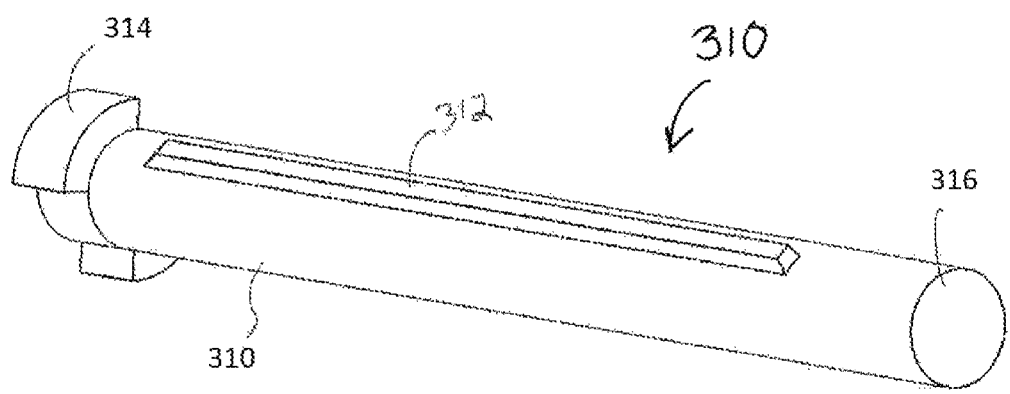
FIG. 7 is a perspective view of a gear key.

In some embodiments, described in FIGS. 6A, 6B, and 7, the actuator mechanism 310 is a key gear and matching base. FIG. 6A displays a portion of one embodiment of the handle assembly 300 (shown in FIG. 2), including the needle drivers 320. The needle drivers 320 are attached to an actuator base 322 which engages with the actuator mechanism 310 (see also FIGS. 2, 7).

FIG. 6B shows a cross-sectioned at the plane indicated by B-B' in FIG. 6A, in which the actuator base has been opened on a line from B to B'. In one embodiment, the actuator base 322 may include slots 324 and a locking mechanism 326 (FIG. 6B).

FIG. 7 displays one embodiment of the action stage mechanism indicated generally at 310, which in the present example comprises a gear key. The gear key or action stage mechanism 310 includes ridges 312 which engage with the slots 324 of FIG. 6B, and arms 314 which engage with the locking mechanism 326 of FIG. 6B. The gear key 310 is attached to the handle 360 (shown in FIG. 2).

Taken together then, the handle 360 (FIG. 2) is used to push, pull, and rotate the gear key 310. When the trocar assembly 200 (FIG. 2) is being used with any type of cannula 110 (shown in FIG. 2) to create an opening in the patient's tissue and prior to deploying the needles 330 (FIG. 3), the arms 314 of the gear key 310 may be, for example, aligned with the base 322 of the needle driver 320 and the ridges 312 are engaged with the slots 324 so that the arms 314 can slide through the base 322 without engaging the locking mechanism 326. When a user wishes to engage the locking mechanism 326, the practitioner twists the handle 360, turning the key gear 310 in the actuator base 322. This unlocks the ridges 312 from the slots 324, and allows the practitioner to press down to engage the locking mechanism 326. In turn, this pushes the needle drivers 320 forward, pressing the needles 330 (FIG. 3) and the anchors 340 (FIG. 3) out, away from the trocar shaft or obturator shaft 210 (FIG. 2), and into a patient's tissue. The anchors 340 are thus driven through the patient's tissue and into a cavity such as the abdominal cavity 5 (FIG. 1), where the anchors 340 are prevented from moving backwards into the tissue due to the connection of the suture 350 at the midpoint of each anchor 340.

It will be appreciated that a key gear is only one possible means of accomplishing the functionality of the action stage mechanism 310 and locking mechanism 326. For example, some embodiments include a guide pin, cams, and springs, similar to the mechanisms employed in a click pen. Additionally, in some embodiments the action stage mechanism 310 may be adapted to provide for three or more modes of action, by supplying a track of additional grooves and ridges or other means known to one of skill in the art, in order to allow a user to deploy, for example, a depth gauge or stopper (described in further detail below, especially FIG. 8.)

One advantage supplied by the combination of an action stage mechanism 310 and locking mechanism 326 is that the trocar assembly 200 may be deployed to 'preclose' the wound, before the surgery takes place. If desired, the entire obturator shaft 210 (FIG. 2) may be guided out of the patient's tissue after deployment of the needles, wires, or probes 330, leaving the cannula 110 of choice inside the patient, removing the needles 330 but leaving the two anchors 340 on approximately opposite sides of the opening in the patient's tissue, each with a length of suture 350 extending therefrom.

The suture thread 350 (FIG. 3) may be spooled from the suture spool or cavity 230 as the trocar shaft 210 is withdrawn, so that a practitioner is left with an open cannula 110 with two or more suture threads 350 extending up through the cannula 110 and attached to the trocar shaft 210. The trocar shaft 210 can be laid aside, suture threads 350 still attached, and surgical instruments can be inserted into the cannula 110 alongside the suture threads 350 to perform the surgery.

When the clinician wishes to close the opening that was made in the patient's tissue, the cannula 110 is simply withdrawn, the practitioner cuts the suture threads 350, forms a slideable knot in the lengths of suture 350 left outside the patient, and slides the knot down with a gloved finger, until the knot pulls the embedded anchors 340 together, thus closing the abdominal fascia 8 (FIG. 1).

In addition to this 'preclose' option, a practitioner may insert the trocar or obturator shaft 210 (FIG. 2) into any standard cannula 110 desired, and close the abdominal fascia 8 after a surgery is complete. In order to accomplish this, the cannula 110 is slightly withdrawn past the edge of the abdominal fascia 8, the trocar shaft 210 is inserted, and the locking mechanism 326 (FIG. 7) is engaged to deploy the needles 330 and anchors 340. Then the wound may be closed as previously described.

Figure 8:
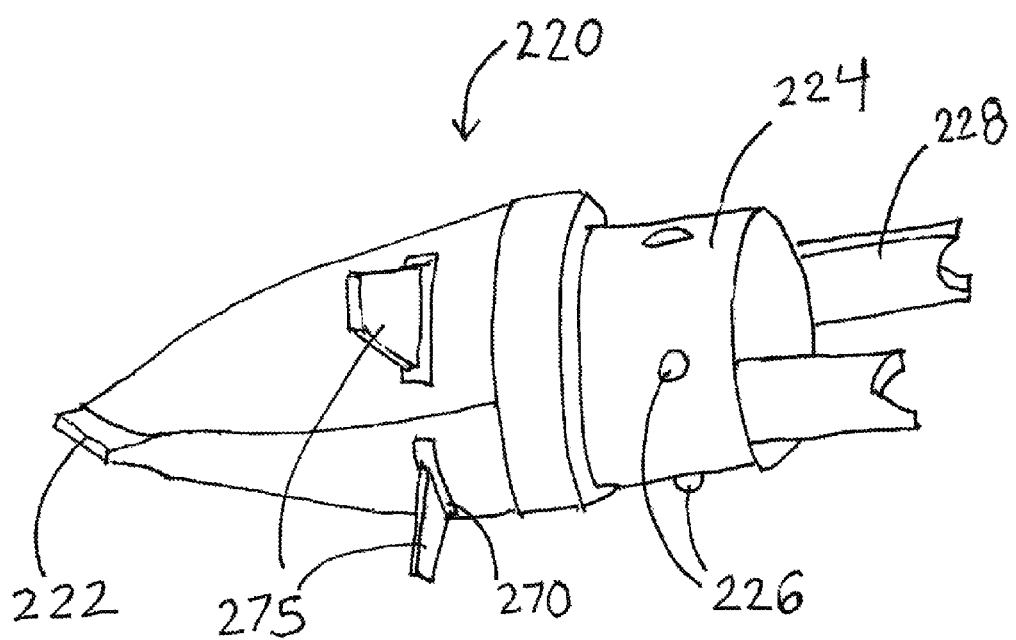
FIG. 8 is a perspective view of a tip for a trocar.

FIG. 8 details the tip, generally at 220, of the trocar or obturator shaft 210 (shown in FIG. 2). In some embodiments the tip 220 may include a bladeless point 222. The use of a bladeless tip minimizes abdominal wall and vessel trauma by separating and pushing the tissue fibers apart along natural lines instead of cutting the tissue. Bladeless tips (which might be, e.g., 1 mm×4 mm) create 41% smaller fascial defects than bladed trocars. The tip 220 may also include a neck 224 which fits into the first distal end 202 (shown in FIG. 2) of the trocar body 210 (shown in FIG. 2), where the neck 224 may have a smaller diameter than the trocar body 210 so that the connection between the tip 220 and the trocar body 210 (shown in FIG. 2) is flush. The neck 224 may include one or more protrusions 226 which fit into matching depressions in the trocar body or shaft 210 to ensure a tight connection between the tip 220 and the trocar body 210. The neck 224 may also include extensions 228 that fit into matching slots 208 (shown in FIG. 9) in the trocar body 210 and which may include rounded cutouts to support the suture spool 230 (FIG. 2). Embodiments in which the tip 220 is formed as a piece with the rest of the trocar shaft 210 will, of course, lack the neck 224 and other attachment portions.

The trocar tip 220 may be formed from a clear plastic, thus enabling a practitioner to determine when the trocar tip 220 breaches the abdominal fascia 8 (presuming that a laparoscope with a light has already been inserted into the abdominal cavity.) Alternatively, the trocar tip 220 may also be supplied with a depth gauge 270, which may be for example one or more flanges, feet, or wings 275. In some embodiments, the flanges 275 may be springloaded; two or more flanges 275 may be present, or the flanges 275 may be formed in the shape of a single, compressible annular ring or ridge. When the trocar tip 220 pierces the abdominal fascia and reaches a desired depth, such that the needle openings 255 (shown in FIGS. 2, 3) have not yet passed through all the layers of the abdominal fascia but the tip of the obturator has passed through these layers, the flanges 275 extend, preventing the trocar shaft 210 from being drawn out until the needles are deployed. In embodiments in which the action stage mechanism 310 and locking mechanism 326 (FIGS. 6A, 6B, and 7) allow for a third stage or mode of action, the action of the springloaded flanges 275 may be manually lockable or unlockable by the user, via twisting the handle to the desired setting, depressing a button or lever, and the like.

Figure 9:
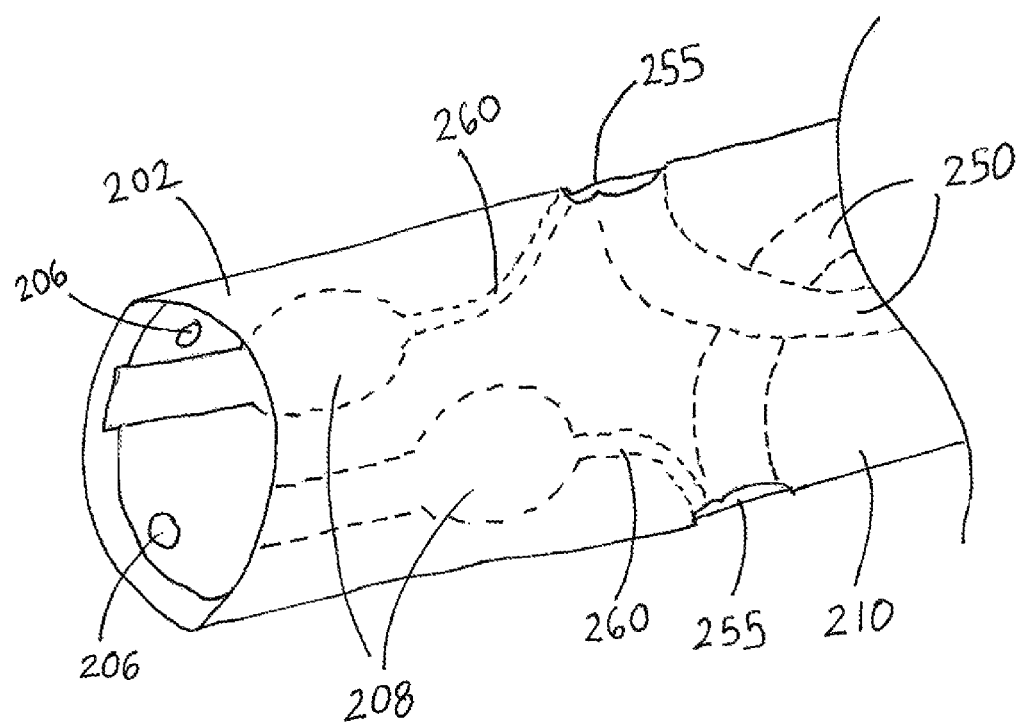
FIG. 9 is a perspective view of an end of a trocar body.

FIG. 9 displays the first, distal end 202 of the trocar shaft 210, where the suture spool 230 (shown in FIG. 10) may be located. The first end 202 may comprise notches or hollows 208 in which a spool 230 can be placed. It will be appreciated that in some embodiments, the suture spool 230 may be instead a hollow in which suture thread 350 is folded or coiled, and the suture spool may be located elsewhere in the trocar shaft 210 or handle assembly 300.

In the embodiment shown in FIG. 9, suture thread 350 (shown in FIG. 2) from the spool 230 may feed up through the suture channels 260, which terminate at or near the needle openings 255. The anchor channels 250 likewise terminate at the needle openings 255, thus when the anchors are deployed, they draw out suture thread 350 from the spool 230 which is held in the notches or hollows 208.

In various alternative embodiments, instead of using the suture spool 230, the length of suture 350 may instead be stored in another manner in association with the trocar body 210, for example packed into the space behind the tip 220 or in the central portion of the trocar body 210 (e.g. coiled or folded in a manner that prevents tangling), in other embodiments the suture 350 is fed through the anchor channels 250 back towards second end 204 of the trocar body 210.

Figure 10:
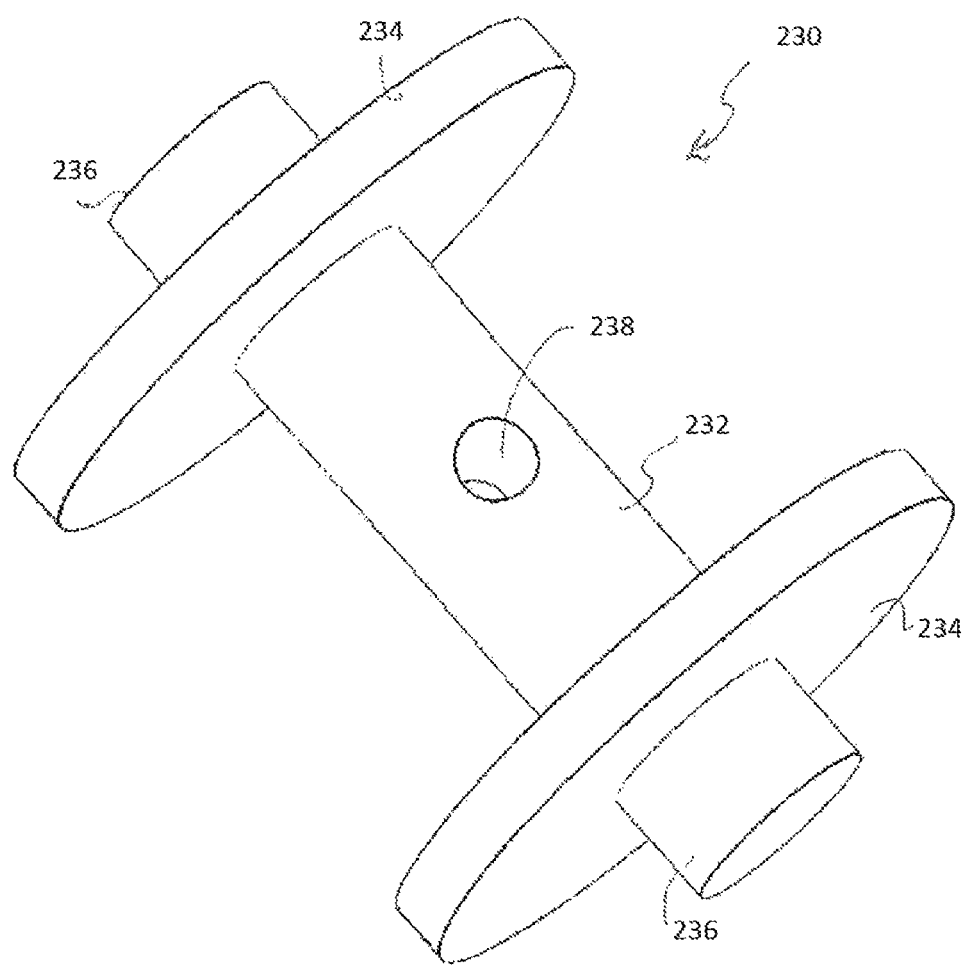
FIG. 10 is a perspective view of a suture spool.

FIG. 10 shows a suture spool 230 including an axle 232 with two flat wheels 234 and extensions 236 adjacent to the wheels 234. The axle 232 may also include an opening 238 into which suture thread 350 may be inserted. In use, one or more lengths of suture 350 are inserted into the opening 238 and wound around the axle 232 of the suture spool 230 between the wheels 234. The spool 230 is inserted into the first end 202 (shown in FIG. 9) of the trocar body 210 (shown in FIG. 9), or any other location on the trocar body 210 or handle assembly 300 (shown in FIG. 2), and the tip 220 (shown in FIG. 8) is placed over the first end 202, engaging the extensions 236 of the suture spool 230. The length(s) of suture 350 then extend into the suture channel(s) 260 (shown in FIG. 9) as described above. In use, the suture 350 may either be attached or tied to the axle 232, or may be releasable when unwound to such a length that the anchors 340 have been inserted into the tissue and the trocar 200 (shown in FIG. 2) is withdrawn.

Figure 11B:
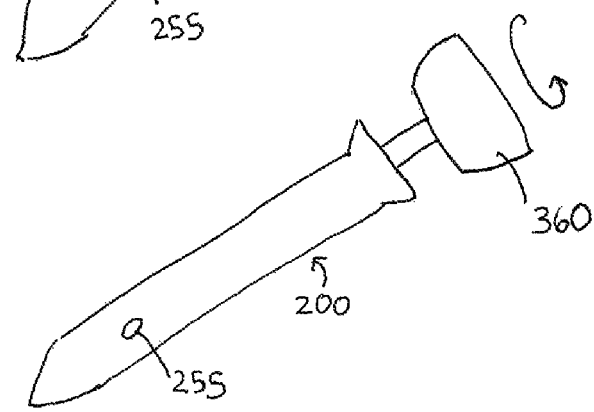
FIG. 11B-11C is a series of perspective views of a trocar illustrating steps for deploying suture anchors for a self-closing laparoscopic port.
Figure 11C:
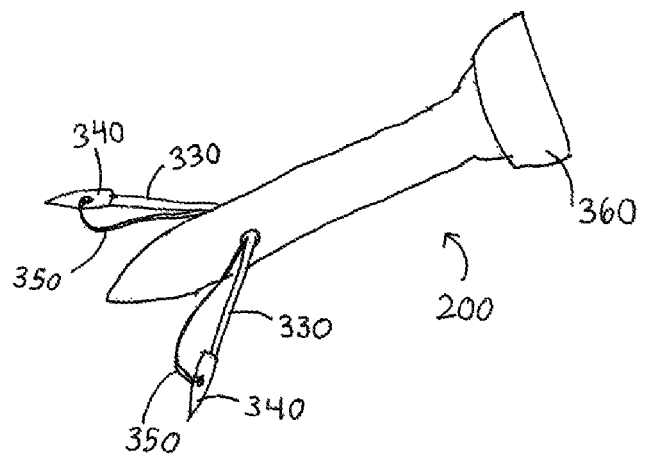

Referring now to FIGS. 11A-11C, there is shown the trocar or obturator 200 at various points of the deployment procedure; FIG. 11B shows the handle 360 being pulled (so that the gear key 310 (shown in FIGS. 6A, 6B, and 7) is slid at least partway out of the base 322 (shown in FIGS. 6A, 6B, and 7)); the handle 360 is rotated (e.g. approximately 90° clockwise) so that the arms 314 (shown in FIGS. 6A, 6B, and 7) are engaged with the locking mechanism 326 (shown in FIGS. 6A, 6B, and 7). The clinician can then push on the handle 360 such that the force of the handle 360 is transmitted to the gear key 310 (shown in FIGS. 6A, 6B, and 7), then to the needle driver 320 (shown in FIGS. 6A, 6B, and 7), then to the needles 330, and eventually to the anchors 340 (FIG. 11C). As the anchors 340 are pushed away from the trocar or obturator 200, the anchors 340 draw out suture thread 350 from the suture spool 230 contained inside the trocar 200.

One advantage of various embodiments of the present invention is that, if a practitioner desires only to close a wound or opening, the trocar 200 may be inserted into the wound or opening without need for a cannula at all, thus avoiding further tissue damage.

Figure 12:
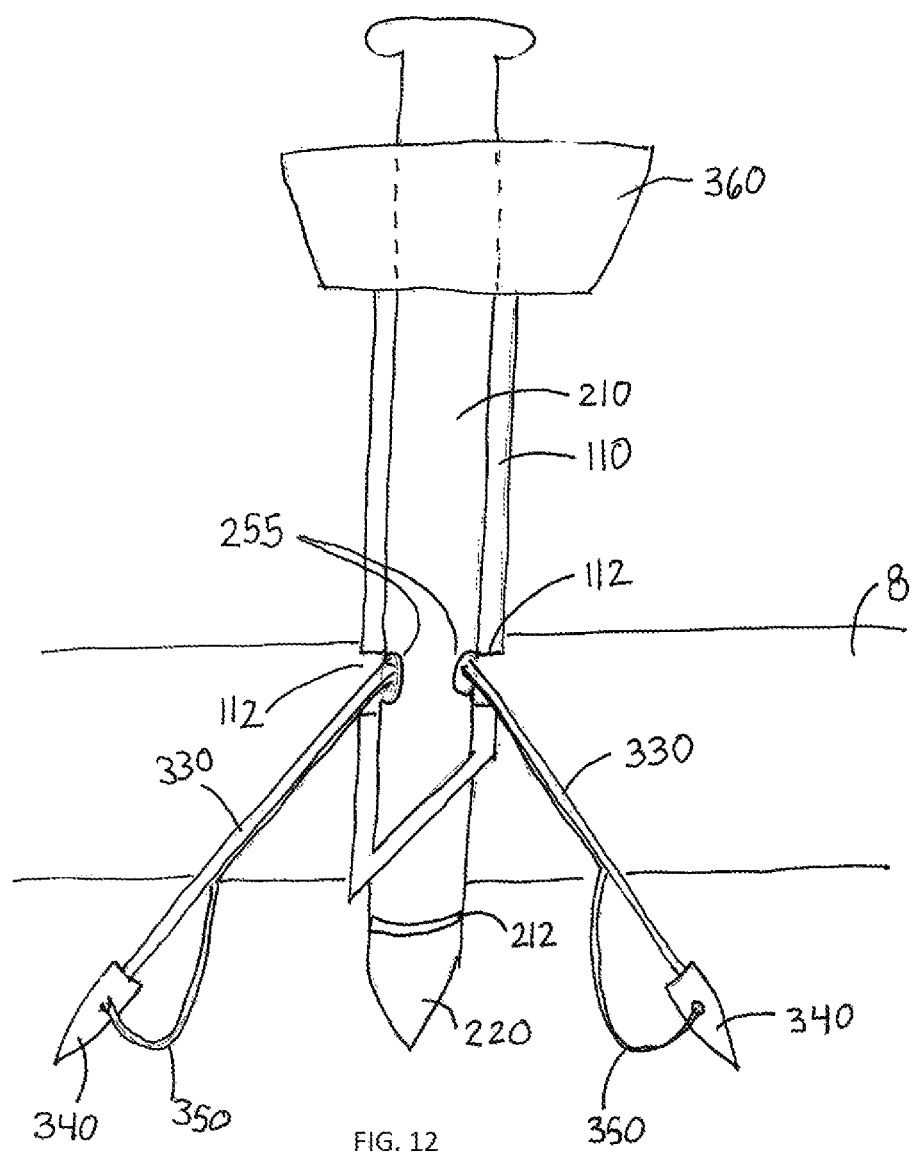
FIG. 12 is a side view of a self-closing laparoscopic port in which anchors have been deployed into a patient's tissue, through holes provided in the cannula tube.

FIG. 12 displays a cut away view of a trocar shaft 210 and a cannula 110 with needles 330 deployed through a patient's tissue or abdominal fascia 8. In various embodiments, the cannula 110 may include one or more exit openings 112 matched to the openings 255 through which the anchors 340 project from the trocar body 210. The exit openings 112 may be circular, oval, or other suitable shape to permit the anchors 340 to exit from the trocar body 210 without being obstructed. The exit openings 112 may be somewhat larger than is strictly needed for the size of the anchors 340 to permit some leeway in alignment between the cannula 110 and the trocar shaft 210. The exit openings 112 may also be aligned (in conjunction with the depth guidance line discussed below) slightly below the openings 255 through which the anchors 340 exit from the trocar body 210 due to the downward angle of exit of the anchors 340.

The cannula 110 and/or the trocar body 210 may also include a depth guidance line 212 (shown on the trocar body or shaft 210 in FIG. 12) to assist the clinician in setting the trocar 200 at the correct depth before the anchors 340 are deployed (FIG. 12). The clinician can visualize the depth guidance line 212 from within the patient's body cavity using a camera or laparoscope (see, e.g. FIG. 1). The camera is generally inserted through a smaller port (e.g. 5 mm diameter) than the trocar (e.g. 15-25 mm diameter) and so the camera port typically does not need to be closed with sutures following surgery. In other embodiments, the cannula 110 may also include a depth guidance line, depending on the overall length of the cannula 110 relative to the thickness of tissue. The depth guidance line may be printed with a biocompatible ink or dye (generally FDA-approved for use in humans) and/or may include a raised or indented portion of the cannula 110 or trocar body 210 to facilitate visualization. It will be appreciated that, particularly in embodiments which include a mechanical depth gauge (e.g. 270 in FIG. 8), a painted or printed depth gauge is likely unnecessary, although potentially still useful.

In various embodiments the anchors 340 and needles 330 project from the trocar body 210 at approximately 45° angles, although other angles are also possible. As shown in FIG. 12, when the cannula 110 and trocar 200 are set at the correct depth, the deployed anchors 340 penetrate the patient's tissue (including, for example, the transversalis fascia) and are lodged in the body cavity. In one embodiment the anchors 340 are located approximately 1 cm from the exterior of the wound opening created by the trocar 200. When the needles 330 are retracted, the anchors 340 and suture 350 will remain in place, permitting the clinician to close the opening made by the trocar assembly 200.

FIG. 12 details one means of using the trocar or obturator shaft 210 with a cannula 110 equipped with exit openings 112, but it should be appreciated that the principles of the invention disclosed herein can be applied to a trocar configured for any type of cannula, including ones equipped with irrigation, aspiration, or lighting. These standard cannulas sometimes lack suitable exit openings 112, through which a needle 330 and anchor 340 can be passed. However, the trocar shaft 210 functions equally well with any cannula which is sufficiently shorter than the trocar shaft 210, so that the standard cannula does not cover any of the openings 255 in the trocar shaft 210.

Although the description and drawings provided herein recite a self-contained port-closing trocar 200 having two anchors 340, two needles 330, etc., in various embodiments other numbers of anchors, needles, and related components are also possible. For example, three, four, or more anchors, needles, etc. may be used on ports having larger openings, both because the opening is larger and may require more sutures to repair and because a larger opening and trocar body would be available to accommodate the additional space required for three or more channels in the trocar body.

In some embodiments the clinician may make a larger opening, for example an elongated opening to permit removal of tissue, requiring more than one set of sutures to close the surgical opening. In this case, a trocar 200 and associated cannula 110 may be inserted more than once at different locations along the surgical opening to place sutures at multiple locations. The same trocar 200 may be used for each set of sutures, once reloaded with additional anchors 340 and suture thread 350, or a new trocar 200 may be used for inserting each set of sutures.

Various embodiments of the self-closing laparoscopic trocar or obturator 200 (shown in FIG. 2) disclosed herein may be used in various procedures including but not limited to laparoscopic surgery in the abdomen or thorax, and may be used for placing anchors in connection with other medical procedures such as placement of feeding tubes in a patient's stomach, or the closure of hernias opened accidentally. Patients may include humans or other animals, with suitable accommodations being made to the dimensions of the components for the type of patient and the part of the anatomy that is being anchored or sutured.

In general the trocar body or shaft 210 may be designed to be compatible with standard sizes of cannulas 110 and the handle 360 and other components are designed for comfortable and ergonomic use. For example, the handle 360 may be sized (e.g. in some embodiments the handle 360 is a cylindrical rod of approximately 36 mm in length and 33 mm in diameter) to fit into a user's palm and the trocar/cannula unit may be designed so that not more than 8 psi of force is required for insertion. The trocar body 210 may be generally cylindrical, for example 10 mm in diameter and 20 cm in length, although dimensions will vary depending on the application and the type of cannula that is being used, where standard inside diameters for cannulas include 8, 10, 12, and 15 mm diameters. The handle 360 may be made of a variety of suitable materials including, for example, polystyrene, whereas the trocar body 210 and related components may be made of materials such as ABS (Acrylonitrile butadiene styrene) plastic. It may be advantageous for the trocar body 210 to be made of clear material—as the interior of the abdomen is brightly lighted once the laparoscopic camera is inserted, the practitioner can more accurately determine when the trocar tip 220 has breached the abdominal fascia 8.

Figure 13:
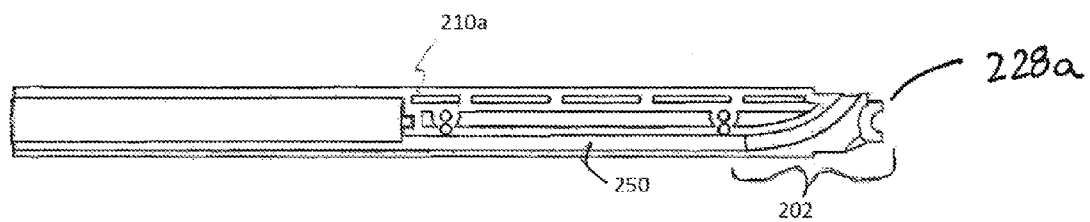
FIG. 13 is a side view of a trocar body half piece.
Figure 14:
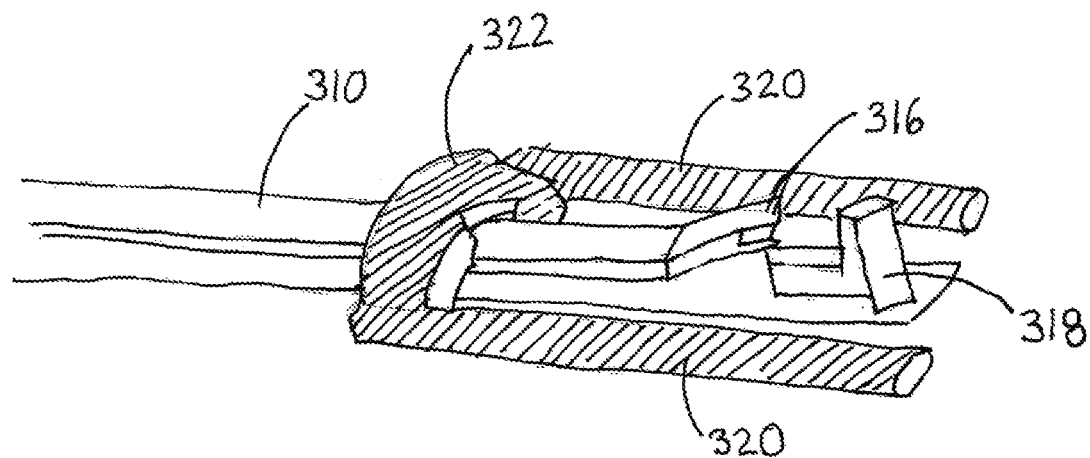
FIG. 14 is a perspective view of a trocar body half piece with a needle driver and a gear key.
Figure 15:
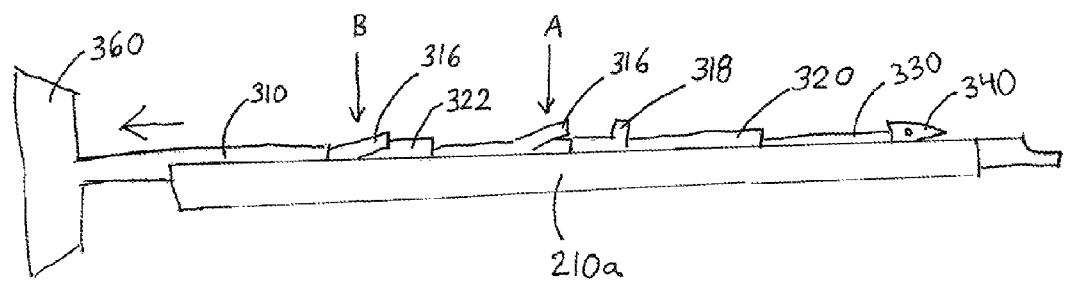
FIG. 15 is a side view of a trocar body half piece with a needle driver and a gear key showing a locking mechanism for engaging the needle drivers with the handle.

Referring now to FIGS. 13, 14, and 15, there is displayed an alternate embodiment in which the trocar body 210 may be formed as two pieces, for example two identical pieces such as a trocar body half piece 210a shown in FIG. 13, which can be brought together to form a complete trocar or obturator body 210 (shown in FIG. 12), thus reducing costs of manufacture. Each trocar body half piece 210a includes a half-cylindrical portion which accommodates the needle driver base 322 as well as the gear key or action stage mechanism 310.

Each trocar body half piece 210a may also include an anchor channel 250, each of which accommodates a needle driver 320. The anchor channel 250 on each trocar body half piece 210a is curved at the end in order to guide the needles 330 and anchors 340 out of the trocar and into the tissue. Instead of being cylindrical, the needle drivers 320 in some embodiments may be rounded on one side (i.e. the side which fits into the anchor channel 250) and flattened on the other side, as shown in FIG. 13. In addition, the first end 202 of each trocar body half piece 210a may be modified (e.g. including a step portion 228a as shown in FIG. 13) for attachment of a tip 220 (Shown in FIG. 2), and may include rounded profiles to hold a suture spool 230 within the tip 220.

FIGS. 14 and 15 show an alternative mechanism for lockably engaging the handle 360 with the needle driver base or actuator base 322 and the needle drivers 320. In some embodiments, the gear key 310 includes a pair of outwardly-biased legs 316 which are flexibly attached to the shaft of the gear key 310. The legs 316 are initially located (position A in FIG. 15) between the needle driver base 322 and the distal end of the trocar body 210.

When the handle 360 is pulled away from the trocar body 210, the gear key 310 slides through the needle driver base 322 until the legs 316 are pulled completely through, extend away from the shaft of the gear key 310, and engage with the needle driver base 322 (position B in FIG. 15). With the legs 316 of the gear key 310 engaged with the needle driver base 322, the handle 360 is then pushed back towards the trocar body half piece 210a, advancing the needle drivers 320 distally and driving the needles 330 and anchors 340 out of the trocar and into the tissue.

In some embodiments, the gear key 310 includes a stop 318 which allows the needle driver base or actuator base 322, needle drivers 320, and needles 330 to be retracted once the anchors 340 (shown in FIG. 2) have been inserted into the tissue. The stop 318 also prevents the gear key 310 from being completely disengaged from the needle driver base 322.

Figure 16:
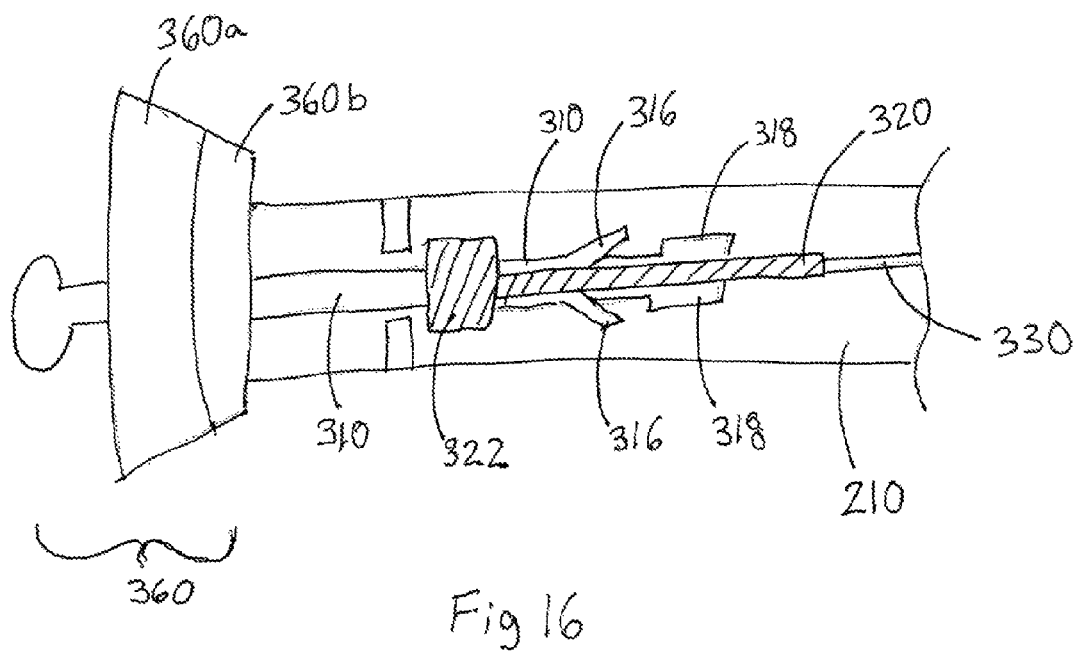
FIG. 16 is a side view of a trocar body with a modified handle.
Figure 17C:
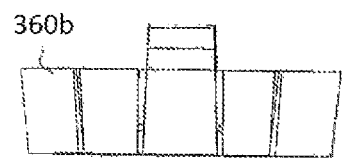
FIGS. 17A-17D show side (17A, 17B) and top (17C, 17D) views of the first (17A, 17C) and second (17B, 17D) portions of the modified handle.
Figure 17D:
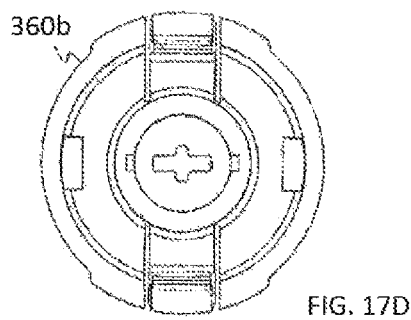
Figure 17A:
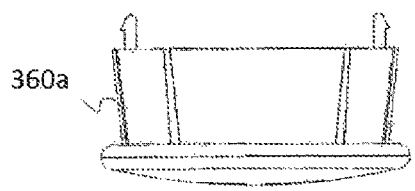
Figure 17B:
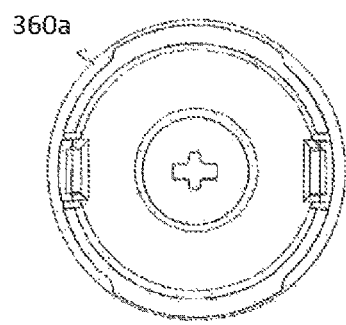

Referring now to FIG. 16, there is shown a cut-away side view of an assembled device according to FIGS. 14 and 15, in which two half-pieces 210a (shown in FIG. 15) are joined to create a trocar body 210. The shaded portion, driver base 322 and needle driver 320, is prevented from being drawn proximally towards the handle 360. Thus, when the first handle portion 360a is twisted and drawn back, the flexible legs 316 are pulled through the driver base 322. When the first handle portion 360a is then pushed back in, the legs 316 catch on the driver base 322 and push it, along with the attached needle drivers 320 and needles 330, distally towards the tip (omitted for clarity) of the trocar 200. The stop 318 is fixedly attached to the walls of the trocar half-pieces (omitted for clarity), and thus the driver base 322 will hit the stop 318 and will not advance distally any farther.

In certain embodiments, a handle 360 facilitates engagement of the legs 316 with the needle driver base or actuator base 322 and driving of the needles 330 and anchors 340 out of the trocar and into the tissue. The modified handle 360 includes a first handle portion 360a and a second handle portion 360b. The first handle portion 360a engages with the end of the shaft of the gear key or other action stage mechanism 310 and is removably engaged with the second handle portion 360b. The second handle portion 360b is engaged with the trocar body 210 and includes a central opening through which the gear key or other action stage mechanism 310 may slide freely.

It will be appreciated that first handle portion 360*a* and second handle portion 360*b* may be removably engaged in any means known to one of skill in the art, such as clips, interlocking ridges, or the like, as better shown in FIGS. 17A-17D.

In the embodiment as shown in FIGS. 13-17D, a clinician or other user disengages the first handle portion 360*a* from the second handle portion 360 and pulls the first handle portion 360*a* away from the second handle portion 360*b*. As discussed above, the gear key 310 is pulled out until the legs 316 are drawn completely through and engage with the needle driver base 322 (position B in FIG. 15). At this point the first handle portion 360*a* is pushed towards the second handle portion 360*b* in order to advance the needle drivers 320 through the anchor channels 250 and drive the needles 330 and anchors 340 out of the trocar and into the tissue.

In various embodiments, the anchor channels 250 curve and terminate at openings which are located on the trocar body 210 further down the first distal end 202 and closer to the tip 220 than what is shown, for example, in FIG. 3. In certain embodiments, when the locations of the openings at the ends of the anchor channels 250 are located sufficiently far down towards the first end 202, the tip 220*a* may be modified to include openings 229 (FIG. 18) through which the needles 330 and anchors 340 may exit (see FIG. 3). One advantage of locating the exit points of the anchor channels 250 further down the trocar body is that it facilitates the use of the disclosed trocar with standard cannulas currently available on the market.

Figure 18:
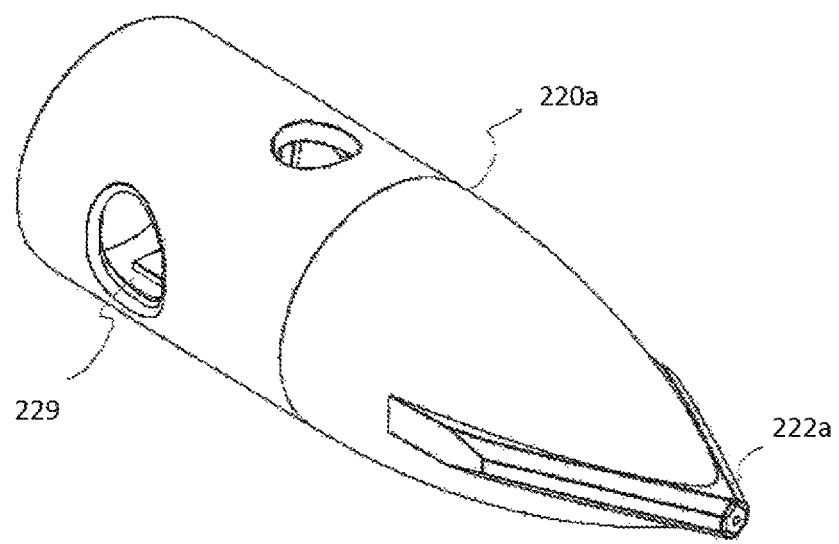
FIG. 18 shows a construction of a tip for use with a trocar as disclosed herein.

In some embodiments, an alternative tip 220*a* includes not only the openings 229 but also a modified bladeless tip 222*a*, as shown in FIG. 18.

In some embodiments, as shown in FIG. 19A-B, the wings or feet 275 may be arrayed to emerge from the trocar or obturator shaft 210 (shown in FIG. 3) or the trocar tip 220 from vertical storage. In some embodiments, the wings or feet 275 may be rotationally affixed to a hub 276, which may be springloaded or flexibly biased, so as to extend the wings automatically when the hub is drawn distally. The extension of the wings 275 may be limited by a wing stopper 277, which prevents the wings from being drawn too far back and entering the body of the trocar. The extension of the wings, feet, or blunt blades 275 may be controllable by, for example, the practitioner's use of a different rotationally-selected track of the action stage mechanism 310 (discussed in FIG. 2,) or by a dedicated button or lever, or any other means known by one of skill in the art.

Thus, the invention provides, among other things, a self-contained port closing trocar obturator. Various features and advantages of the invention are set forth in the following claims.

What is claimed is:

1. A port-closing obturator, comprising:
   an elongated body having a first end, a second end opposite the first end, and a side wall including opposing first and second sides between the first end and the second end, the body further including at least two channels therein, each of the channels originating near the second end, running parallel to a longitudinal axis of the elongated body and adjacent to the first or second side of the elongated body, and curving towards and forming an opening in an opposing first or second side near the first end;
   at least two needles, each disposed within one of the at least two channels; and
   a handle engageable with the second end of the elongated body, the handle having at least two needle drivers coupled thereto, each needle driver being engageable with one of the at least two channels and engageable with an end of a needle.

2. The port-closing obturator of claim 1, wherein each of the at least two needles comprises a free end disposed near an opening at the side wall.

3. The port-closing obturator of claim 2, further comprising at least two anchors, each of the at least two anchors associated with the free end of one of the at least two needles.

4. The port-closing obturator of claim 3, further comprising a length of suture attached to each of the at least two anchors.

5. The port-closing obturator of claim 4, wherein selectively engagement the handle with the second end of the elongated body drives each of the at least two needles through an opening in the side wall and out of the elongated body.

6. The port-closing obturator of claim 4, further comprising a suture spool disposed at the first end of the elongated body, wherein at least a portion of the length of suture is wound around the suture spool.

7. The port-closing obturator of claim 5, wherein each of the at least two needles is driven through respective openings on the first and second sides of the side wall of the elongated body.

8. The port-closing obturator of claim 7, wherein each of the at least two needles exits at a fixed angle of between about 35 degrees relative to the elongated body and about 60 degrees relative to the elongated body.

9. The port-closing obturator of claim 8, wherein pulling the handle out of the second end of the elongated body retracts each of the at least two flexible needles into one of the at least two channels.

10. The port-closing obturator of claim 1, wherein the end of the elongated body comprises a bladeless tip.

11. The port-closing obturator of claim 1, wherein the handle further comprises a gear key, and wherein the gear key either slidingly engages with the needle drivers or lockingly engages with the needle drivers.

12. A self-closing laparoscopic port system comprising:
   a self-closing obturator, the obturator including an elongated body having a first end, a second end opposite the first end, a longitudinal axis, and a side wall including opposing first and second sides between the first end and the second end, the body further including at least two channels therein, each of the channels originating near the second end, running parallel to the longitudinal axis of the elongated body adjacent the first or second first side, and curving towards and forming a obturator opening in the side wall opposing the first or second side near the first end, at least two needles, each disposed within one of the at least two channels, and
   a handle engageable with the second end of the elongated body, the handle having at least two needle drivers coupled thereto, each needle driver being engageable with one of the at least two channels and engageable with an end of a needle; and a cannula configured to receive the self-closing obturator.

13. The self-closing laparoscopic port system of claim 12, wherein the cannula comprises two openings along a length thereof, the cannula openings configured to align with the obturator openings in the body.

14. The self-closing laparoscopic port system of claim 13, wherein at least one of the cannula and the self-closing obturator comprises a depth gauge.

15. The self-closing laparoscopic port system of claim 14, wherein each of the at least two flexible needles has a free end disposed near the obturator opening.

16. The self-closing laparoscopic port system of claim 15, further comprising at least two anchors, each of which is associated with the free end of one of the at least two flexible needles.

17. The self-closing laparoscopic port system of claim 16, further comprising a length of suture attached to each of the at least two anchors.

18. The self-closing laparoscopic port system of claim 17, wherein the handle is configured to selectively engage the second end of the elongated body such that the at least two flexible needles are driven through the obturator opening and out of the elongated body.

19. The self-closing laparoscopic port system of claim 18, wherein each of the at least two flexible needles is driven through one of the cannula openings.

20. A handle assembly and obturator for a self-closing trocar, comprising: a handle having at least two needle drivers coupled thereto, each needle driver being engageable with an end of a needle; at least two flexible needles, each needle having a first end and a second end, the first end being coupled to one of the at least two needle drivers; and at least two anchors, each anchor being removably coupled to the second end of the at least two flexible needles;

the obturator having an elongated body having a first end, a second end opposite the first end, and a side wall including first and second sides between the first end and the second end, the body further including at least two channels therein, each of the channels originating near the second end, having a straight portion running parallel to a longitudinal axis of the elongated body and adjacent to a first or second side of the elongated body, and a curved portion curving towards and forming an opening in the opposing first or second side near the first end.

21. The handle assembly of claim 20, further comprising a length of suture attached to each of the at least two anchors.

22. The handle assembly of claim 21, wherein the handle further comprises a gear key, and wherein the gear key either slidingly engages with the needle drivers or lockingly engages with the needle drivers.

23. A medical device for insertion through an abdominal wall comprising:
an obturator, the obturator comprising:
a proximal end configured for handling by a user;
a distal end comprising a tip configured to form an insertion wound in the abdominal wall; and
a shaft extending between the proximal end and the distal end, wherein the shaft comprises:
at least two channels therein, each of the channels originating proximal to the proximal end, running parallel to the shaft on a first or second side of the shaft, and curving towards and forming an opening in the side wall proximal to the distal end on a second side of the shaft opposing the first or second side of the shaft; and
a handle having at least two needle drivers coupled thereto, each of the at least two needle drivers being engageable with one of the at least two channels and configured to engage a needle.

24. The obturator of claim 23, further comprising at least two needles, each of the at least two needles disposed within one of the at least two channels, and wherein each of the at least two needles comprise a proximal end for connection to one of the at least two needle drivers and a distal end.

25. The obturator of claim 23, further comprising an expandable structure which when expanded increases contact with fascia tissue facing the an abdomen, the expandable structure comprising a closed configuration for insertion or removal of the obturator, and an open configuration for preventing the obturator from being pulled in a proximal direction.

* * * * *